(12) United States Patent
Iwamoto et al.

(10) Patent No.: US 8,318,658 B2
(45) Date of Patent: Nov. 27, 2012

(54) CELL CALCIFICATION SUPPRESSING PROTEINS, AND GENES OF THE PROTEINS

(75) Inventors: Masahiro Iwamoto, Osaka (JP); Yoshinobu Higuchi, Shizuoka (JP); Maurizio Pacifici, Philadelphia, PA (US); Joel Rosenbloom, Philadelphia, PA (US)

(73) Assignee: University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/353,382

(22) Filed: Jan. 14, 2009

(65) Prior Publication Data

US 2009/0275030 A1 Nov. 5, 2009

Related U.S. Application Data

(62) Division of application No. 10/851,328, filed on May 24, 2004, now Pat. No. 7,494,970, which is a division of application No. 09/902,772, filed on Jul. 12, 2001, now abandoned, and a division of application No. 08/878,177, filed on Jun. 18, 1997, now Pat. No. 6,294,354.

(51) Int. Cl.
*C07K 14/00* (2006.01)
(52) U.S. Cl. .......................... 514/1; 530/350
(58) Field of Classification Search ............... 530/350; 514/1
See application file for complete search history.

(56) References Cited

U.S. PATENT DOCUMENTS 6,294,354 B1 9/2001 Iwamoto et al. ............ 435/69.1

OTHER PUBLICATIONS

Rao et al. 1987; Erg, a human ets-related gene on chromosome 21: alternative splicing, polyadenylation, and translation. Science 237: 635-639.*
Anderson, Nature, 392:25-30 1998.
Chen et al., Molecular and Cellular Biology, pp. 2745-2752 (Aug. 1987).
Dhordian, et al., Mechanism of Development, 50:17-28 (1995).
Duterque-Coquillaud, M. et al. "New human erg isoforms generated by alternative splicing are transcriptional activators" Oncogene, 1993, 8, pp. 1865-1873.
Gerstenfeld, et al., Development Biology, pp. 49-60 (1987).
Higuchi, et al., Journal of the Japan Society of Bone Metabolism, 12(2) (1997).
Hughes, et al., Journal of Virology, pp. 3004-3012 (Oct. 1987).
Iwamoto, et al., Journal of Biological Chemistry, pp. 9645-9652 (May 1993).
Iwamoto, et al., Microscopy Research & Technique, 28:483-491 (1994).
Kato, et al., Endocrinology., 127(1):114-118 (1990).
Kriegler, "Gene Transfer and Expression: A Laboratoru Manual", 1991, pp. 29-56.
Nishikawa et al., Nonviral Vectors in the New Millennium: Delivery Barriers in Gene Transfer 2001 Human Gene Theraa , vol. 12, . . . 861-870.
Potts et al., J. Gen. Viol., pp. 3177-3182 (1982).
Reddy, E. et al. "The erg gene: a human gene related to the ets oncogene" Proc. Natl. Acad. Sci. USA, 1987, 84(17), pp. 6131-6135.
Verma, et al., Nature, 389:239-242 1997.
* cited by examiner

*Primary Examiner* — Karen Cochrane Carlson
(74) *Attorney, Agent, or Firm* — Morgan, Lewis & Bockius LLP

(57) ABSTRACT

This invention provides cell-calcification inhibitory proteins as well as genes encoding the proteins. Based on the discovery of a novel isoform gene of the c-erg gene (herein referred to as "C-11 gene") which is an erg gene derived from chickens, the nucleotide sequence of the gene has been determined, and then the expression of a protein encoded by such gene (herein referred to as "C-11 protein") has been confirmed. Further, it has been discovered that when the c-erg or C-11 gene is introduced into osteoblasts, the calcification of the cells is inhibited.

3 Claims, 12 Drawing Sheets

```
GAATTCCGCGAACGAATAATTATTATTAGCAATTATTAGCGATCAATAATCTTGATCACATT    62

ATG GCA AGC ACT ATT AAG GAA GCA TTA TCA GTG GTG AGT GAA GAC CAG TCC TTG TTT GAG    122
 M   A   S   T   I   K   E   A   L   S   V   V   S   E   D   Q   S   L   F   E     20

TGT GCC TAC GGA TCG CCC CAC CTT GCA AAG ACA GAA ATG ACA GCC TCC TCT TCC AGT GAA    182
 C   A   Y   G   S   P   H   L   A   K   T   E   M   T   A   S   S   S   S   E     40

TAT GGG CAA ACA TCA AAG ATG AGC CCG CGC GTT CCC CAG CAG GAC TGG TTA TCA CAG CCC    242
 Y   G   Q   T   S   K   M   S   P   R   V   P   Q   Q   D   W   L   S   Q   P     60

CCG GCC AGA GTT ACC ATT AAG ATG GAG TGT AAC CCA AAC CAG GTT AAT GGG TCA AGG AAT    302
 P   A   R   V   T   I   K   M   E   C   N   P   N   Q   V   N   G   S   R   N     80

TCA CCT GAT GAC TGC AGC GTG GCA AAA GGA GGG AAA ATG GTT AGC AGT TCA GAC AAT GTT    362
 S   P   D   D   C   S   V   A   K   G   G   K   M   V   S   S   S   D   N   V    100

GGG ATG AAC TAT GGA AGC TAC ATG GAA GAG AAG CAT ATT CCG CCT CCA AAT ATG ACA ACC    422
 G   M   N   Y   G   S   Y   M   E   E   K   H   I   P   P   P   N   M   T   T    120

AAT GAA CGA AGA GTT ATT GTG CCA GCA GAT CCT ACG TTA TGG AGC ACA GAC CAT GTA CGG    482
 N   E   R   R   V   I   V   P   A   D   P   T   L   W   S   T   D   H   V   R    140

CAG TGG CTG GAG TGG GCA GTG AAG GAG TAT GGT CTT CCA GAC GTG GAC ATC TTG TTG TTC    542
 Q   W   L   E   W   A   V   K   E   Y   G   L   P   D   V   D   I   L   L   F    160

CAG AAC ATT GAT GGG AAA GAG TTG TGT AAA ATG ACC AAA GAT GAC TTC CAG AGA CTC ACG    602
 Q   N   I   D   G   K   E   L   C   K   M   T   K   D   D   F   Q   R   L   T    180

CCG AGC TAT AAC GCA GAT ATC CTC CTG TCA CAC CTA CAC TAC CTC AGA GAG ACT CCT TCC    662
 P   S   Y   N   A   D   I   L   L   S   H   L   H   Y   L   R   E   T   P   L    200

CCA CAT TTG ACT TCA GAT GAT GTT GAT AAG GCC TTA CAA AAC TCT CCA CGG TTA ATG CAT    722
 P   H   L   T   S   D   D   V   D   K   A   L   Q   N   S   P   R   L   M   H    220

GCT AGA AAC ACA GGA GGA GCC ACT TTT ATT TTT CCA AAT ACA TCA GTT TAC CCA GAA GCA    782
 A   R   N   T   G   G   A   T   F   I   F   P   N   T   S   V   Y   P   E   A    240

ACG CAA AGA ATA ACA ACA AGG CCA GAT TTA CCT TAT GAG CAA GCG AGG AGA TCA GCG TGG    842
 T   Q   R   I   T   T   R   P   D   L   P   Y   E   Q   A   R   R   S   A   W    260
```

*FIG. 1A*

```
ACG AGT CAC AGC CAT CCC ACT CAG TCA AAA GCT ACC CAA CCA TCA TCT TCA ACA GTG CCC   902
 T   S   H   S   H   P   T   Q   S   K   A   T   Q   P   S   S   S   T   V   P   280

AAA ACA GAA GAC CAG CGT CCT CAG TTA GAT CCT TAT CAG ATT CTT GGA CCG ACC AGC AGC   962
 K   T   E   D   Q   R   P   Q   L   D   P   Y   Q   I   L   G   P   T   S   S   300

CGT CTT GCA AAT CCA GGG AGT GGG CAG ATA CAG CTA TGG CAG TTC CTA CTG GAG CTT CTG  1022
 R   L   A   N   P   G   S   G   Q   I   Q   L   W   Q   F   L   L   E   L   L   320

TCG GAC AGC TCC AAC TCC AAC TGC ATC ACC TGG GAG GGC ACA AAT GGG GAG TTC AAG ATG  1082
 S   D   S   S   N   S   N   C   I   T   W   E   G   T   N   G   E   F   K   M   340

ACA GAC CCT GAT GAA GTG GCT CGG CGT TGG GGA GAG AGG AAA AGC AAA CCT AAC ATG AAC  1142
 T   D   P   D   E   V   A   R   R   W   G   E   R   K   S   K   P   N   M   N   360

TAT GAC AAA CTC AGC CGT GCA CTT CGC TAC TAC TAT GAC AAA AAT ATT ATG ACT AAA GTT  1202
 Y   D   K   L   S   R   A   L   R   Y   Y   Y   D   K   N   I   M   T   K   V   380

CAT GGT AAA CGC TAT GCC TAC AAA TTT GAT TTC CAC GGA ATC GCT CAG GCC CTC CAG CCT  1262
 H   G   K   R   Y   A   Y   K   F   D   F   H   G   I   A   Q   A   L   Q   P   400

CAC CCT CCA GAA TCA TCC ATG TAC AAA TAC CCA TCA GAC CTC CCC TAC ATG AGT TCC TAC  1322
 H   P   P   E   S   S   M   Y   K   Y   P   S   D   L   P   Y   M   S   S   Y   420

CAT GCA CAC CCC CAG AAG ATG AAC TTT GTA GCT CCC CAT CCC CCT GCT TTG CCC GTA ACC  1382
 H   A   H   P   Q   K   M   N   F   V   A   P   H   P   P   A   L   P   V   T   440

TCA TCC AGC TTT TTT GCT GCC CCT AAT CCA TAC TGG AAT TCA CCA ACT GGA GGC ATC TAC  1442
 S   S   S   F   F   A   A   P   N   P   Y   W   N   S   P   T   G   G   I   Y   460

CCC AAT ACC AGG CTG CCA GCT GCT CAT ATG CCT TCC CAT CTT GGC ACC TAC TAC TAA GTG  1502
 P   N   T   R   L   P   A   A   H   M   P   S   H   L   G   T   Y   Y           478

GGGAAAGAAAGAAAGCGCCAAGAAAA                                                       1528
```

FIG. 1B

CELL CALCIFICATION SUPPRESSING PROTEINS, AND GENES OF THE PROTEINS

This is a divisional application of application U.S. application Ser. No. 10/851,328 (filed May 24, 2004, now U.S. Pat. No. 7,494,970) which is a divisional of U.S. application Ser. No. 09/902,772 (filed Jul. 12, 2001, now abandoned), and U.S. application Ser. No. 08/878,177 (filed Jun. 18, 1997, now U.S. Pat. No. 6,294,354) all of which are incorporated herein by reference in their entirety.

BACKGROUND OF THE INVENTION

1. Field of the Invention

This invention relates to cell-calcification inhibitory proteins as well as to genes encoding such proteins.

2. Description of Related Art

Ets genes were first identified as oncogene of avian acute leukemia virus E26. Recently, the family of Ets related genes (Ets gene superfamily) has been found in a host ranging from human to *Drosophila*. It is believed that these genes are a transcriptional modulator which plays a basic, important role in the control of proliferation and differentiation of cells. In contrast, the biological functions of the Ets gene superfamily are hardly known.

SUMMARY OF THE INVENTION

Recently, it has been reported that the Ets related genes (erg) are specifically expressed at the sites of cartilage formation. This indicated the possibility of erg's being involved to some extent in skeleton formation at its initial stages. The present inventors, based on such findings, have accomplished the invention by introducing into osteoblasts, an erg gene derived from chickens (herein referred to as "chicken-erg gene" or "c-erg gene") and by successfully elucidating the functions of the c-erg gene.

BRIEF DESCRIPTION OF THE DRAWINGS

This application contains at least one figure in color. Copies of a patent issuing from the application, which includes color figures, will be available from the United States Patent and Trademark Office upon request and payment of necessary fees.

FIG. 1 illustrates the nucleotide sequence for c-erg cDNA and the deduced amino acid sequence for c-erg protein where the nucleotide sequence lacking the underlined portion of sequence in the figure corresponds to the C-11 gene nucleotide sequence according to this invention.

DESCRIPTION OF THE PREFERRED EMBODIMENTS

Figure 2:
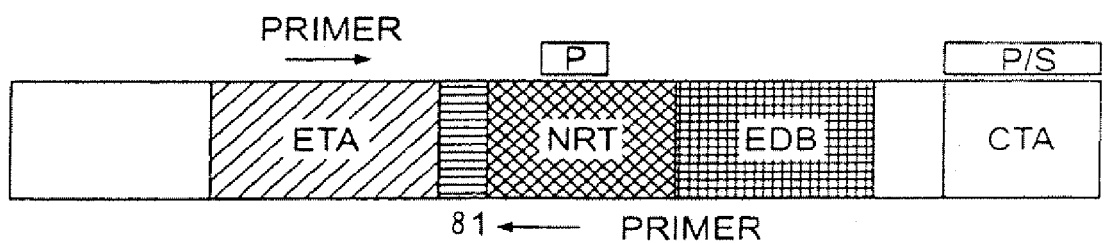
FIG. 2 illustrates the gene domain encoding the c-erg protein, where ETA, NRT, EDB, and CTA represent an erg/ets transcription domain, a transcription repressor domain, an erg/ets DNA-binding domain, and a carboxyl terminal transcription domain, respectively.

The present inventors have discovered a novel isoform gene of the c-erg gene (herein referred to as "C-11 gene" or "C11 gene") which is an erg gene derived from chicken and determined its nucleotide sequence. Furthermore, the inventors have confirmed the expression of a protein encoded by such gene (herein referred to as "C-11 protein" or "C11 protein").

Also, the inventors have discovered that when the c-erg or C-11 gene is introduced into osteoblasts, the calcification of the blasts (or cells) is inhibited.

More specifically, this invention provides a C-11 protein comprising a protein selected from the group consisting of:

(a) a protein comprising an amino acid sequence having SEQ ID NO. 2 (SEQUENCE LISTING), and (b) a protein comprising an amino acid sequence that is derived from the amino acid sequence having SEQ ID NO. 2 by deletion, substitution or insertion of one or more amino acids, said protein having cell-calcification inhibitory activity.

Also, the invention provides a gene encoding the aforementioned protein.

Further, the invention provides a pharmaceutical composition comprising the aforementioned protein as well as provides a pharmaceutical composition intended for a cell-calcification inhibitor.

Also, the invention provides a cell-calcification inhibitor comprising a c-erg protein selected from the group consisting of:

(a) a protein comprising an amino acid sequence having SEQ ID NO. 4 (SEQUENCE LISTING); and (b) a protein comprising an amino acid sequence that is derived from the amino acid sequence having SEQ ID NO. 4 by deletion, substitution or insertion of one or more amino acids, said protein having cell-calcification inhibitory activity.

Further, the invention provides an antibody to the C-11 protein as well as provides an antibody, characterized in that said antibody is a monoclonal antibody.

Still further, the invention provides a method for measuring the calcification of cells comprising the step of measuring the expression of a C-11 gene or a c-erg gene in the cells.

Also, the invention provides the aforementioned method wherein the expression of the gene is measured by the amount of C-11 mRNA expressed in the cells or the amount of c-erg mRNA expressed in the cells using a probe against a DNA sequence specific to the C-11 gene or to the c-erg gene.

Also, the invention provides the aforementioned method wherein the expression of the gene is measured by the amount of expression of the C-11 protein in the cells or the amount of expression of the c-erg protein in the cells.

Further, the invention provides the aforementioned method wherein the expression of the C-11 protein or the c-erg protein in the cells is measured by means of an antibody to the C-11 protein or to the c-erg protein.

Also, the invention provides a method for diagnosing such diseases as OPLL (Ossification of posterior longitudinal ligament) and osteoarthritis which cause pathologic calcification or ossification, said method comprising using the aforementioned method of measurement of the cell-calcification.

In addition, the invention provides a kit for measuring the calcification of cells, comprising either or both of an antibody to the C-11 protein and an antibody to the c-erg protein.

Further, the invention provides a method for screening a substance having cell-calcification inhibitory blocking activity, said method comprising using cells transformed with a gene encoding a protein selected from the group consisting of:

(a) a protein comprising an amino acid sequence having SEQ ID NO. 2 (SEQUENCE LISTING);

(b) a protein comprising an amino acid sequence that is derived from the amino acid sequence having SEQ ID No. 2 by deletion, substitution or insertion of one or more amino acids, said protein having cell-calcification inhibitory activity;

(c) a protein comprising an amino acid sequence having SEQ ID NO. 4 (SEQUENCE LISTING); and (d) a protein comprising an amino acid sequence that is derived from the amino acid sequence having SEQ ID NO. 4 by deletion, substitution or insertion of one or more amino acids, said protein having cell-calcification inhibitory activity.

Furthermore, the invention provides a pharmaceutical composition comprising an erg protein.

Also, the invention provides a pharmaceutical composition comprising an erg gene.

Further, the invention provides a pharmaceutical composition comprising the C-11 protein or the c-erg protein.

In addition, the invention provides a pharmaceutical composition comprising the C-11 gene or the c-erg gene.

Still further, the invention provides a pharmaceutical composition comprising a protein having a consensus amino acid sequence between the c-erg protein and the C-11 protein.

In the present specification and the accompanying drawings where abbreviations are used to describe bases and amino acids. The abbreviations according to the IUPAC-IUB rules or those ascertainable in the art to which the invention pertains are used as set forth in the following:

| Nucleic Acid | |
|---|---|
| DNA | Deoxyribonucleic acid |
| cDNA | Complementary DNA |
| RNA | Ribonucleic acid |
| mRNA | Messenger RNA |
| A | Adenine |
| C | Cytosine |
| G | Guanine |
| T | Thymine |

Isolation and Identification of C-11 Gene

The novel gene according to this invention is an isoform of the c-erg gene derived from chickens. As shown in FIG. 1, when compared with the nucleotide sequence for the c-erg gene, the novel gene has a nucleotide sequence lacking 81 nucleotides from nucleotide 655 to nucleotide 735 (See, SEQ ID NO. 1 in the Sequence Listing). The novel gene according to the invention (or C-11 gene) can be isolated from a variety of cells by a method ordinarily known in the art.

Specifically, total RNA is extracted from chicken embryos, 4-10 days old. After the RNA has been subjected to reverse transcription, the entire translational region of the c-erg gene and C-11 gene can be amplified by the PCR method.

Primers that can be used in PCR, for example, include the following C11B and C11C which amplify both the c-erg and C-11 genes:

```
C11B:  5'-CACATTATGGCAAGCACTATTAAGG-3'

C11C:  5'-CACTTAGTAGTAGGTGCCAAGATGG-3'

C11A:  5'-ATCTTGATCACATTATGCCAAGC-3'.
```

When primers C11B and C11C are each used, two bands, 1446 bp and 1355 bp, appear: the former band corresponds to the c-erg gene and the latter band to the C11-gene, respectively. When primers C11A and C11C are each used, two kinds of DNAs, 1454 bp (c-erg) and 1373 bp (C-11), can be amplified.

In either case, the RT-PCR conditions are as follows: 1 µg of total RNA is subjected to reverse transcription and subsequently to 30 cycles of amplification for one minute at 61° C., for two minutes at 72° C. and for 10 seconds at 95° C. employing 2 units of Tag polymerase to render the products detectable.

In addition, based on the determined nucleotide sequence as described above it is easy to prepare an oligonucleotide probe complementary to an appropriate partial nucleotide sequence thereof. Such probes may be used to enable detection of the C-11 gene by various techniques, C-11 Protein The C-11 protein which can be deduced from the nucleotide sequence for the C-11 gene has an amino acid sequence set forth in SEQ ID NO. 2 in the Sequence Listing.

The C-11 protein can also be expressed in suitable host cells by incorporating the C-11 gene into viral vectors such as adenovirus and chicken retrovirus. See Gene Transfer and Expression: A Laboratory Manual by Michael Kriegler, W.H. Freeman and Company, New York (1991), p 29-56. Further, the amino acid sequence of the proteins thus obtained can be directly determined on a conventional amino acid sequencer.

Furthermore, it is possible to modify the sequence of the C-11 gene set forth as SEQ ID NO. 1 in the Sequence Listing by substitution, deletion or insertion of an arbitrary sequence in said sequence using, for example, site-directed mutagenesis. The site-directed mutagenesis can be repeated one to a few times to prepare C-11 protein variants in which one to a few amino acids are substituted, deleted or inserted as well as gene mutants encoding the variants. Such variants are within the scope of the invention insofar as they possess cell-calcification inhibitory activity.

Also, various methods known in the art may be used to detect the C-11 protein expressed within particular cells. Specifically, representative methods include immunostaining using an antibody to the C-11 protein or a partial protein thereof, a method for the detection of their localization by the use of a fluorescent antibody technique, and a method for measuring the amount of expression of the C-11 protein by means of a radioimmunoassay or ELISA technique on homogenated cells.

c-erg Protein

In a manner similar to that used for the C-11 protein, it is possible to express the c-erg protein set forth as SEQ ID NO. 4 in the Sequence Listing.

Further, variants of the c-erg protein or mutants of their genes can be prepared in a manner similar to that used for the C-11 protein or genes thereof, and can satisfactorily be utilized in this invention insofar as they possess cell-calcification inhibitory activity.

Antibody (Monoclonal Antibody) to C-11 Protein

An antibody to the C-11 protein according to the invention may be that which reacts against either the aforementioned entire C-11 protein or a partial oligopeptide thereof. In additions it is possible to use an antibody conjugated with a suitable substance such as a protein which will impart particular properties to the antibody.

There is no limitation concerning immunological methods in which the aforementioned proteins etc., are used as antigens, and any immunological techniques ordinarily known in the art may be used. Following such methods, a serum containing polyclonal antibodies may be obtained. Further, particular fractions such as IgG can be obtained by purification through ammonium sulfate fractionation or on Protein A Sepharose.

Furthermore, it is also possible to prepare monoclonal antibodies by the cell fusion method.

Cell-Calcification Inhibitory Activity

"Cell-calcification inhibitory activity" caused by introduction of the C-11 gene or the c-erg gene according to the invention, into cells means the inhibition of calcification inductive ability by osteoblasts infected with viral vectors having the aforementioned genes cloned. In this invention the Alizarin Red method may preferably be used to measure the amount of deposition of calcified products which the cells have induced. Also, the von Kossa method (also known as the Alum-carmine method) permits easy discrimination.

Pharmaceutical Compostions and Methods for their Administration

The pharmaceutical compositions according to the invention are characterized by containing the erg protein, erg gene, C-11 protein, c-erg protein, C-11 gene or c-erg gene, each of which has the function to inhibit the calcification of cells as described above. Accordingly, by virtue of the cell-calcification inhibition, those compositions are capable of treating various diseases, more specifically those in which pathological calcification causes ossification such as OPLL and osteoarthritis.

The pharmaceutical compositions provided by the invention are those which contain the aforementioned erg protein, erg gene, C-11 protein, c-erg protein, C-11 gene or c-erg gene. Method for administration of those pharmaceutical compositions are not particularly limited, and conventional administration method are available for use. Specifically, these include local injection, subcutaneous injection and oral administration. In addition, intracellular microinjection or the like may be indicated.

More specifically, by introducing into the cells, the c-erg protein or the C-11 protein in its form bound to a suitable hormone or the like, or in its form as a fused protein, it is possible to have the c-erg or C-11 protein bound to receptors for the hormone, which allows the c-erg or C-11 protein together with the hormone to be taken up within the cells.

EXAMPLE 1

Isolation of C-11 Gene and c-erg Gene

Sterna were separated from chicken embryos, 18 days old and total RNA was then extracted. See, Iwamoto M. et al., Microscopy Research and Technique (1994) 28: 483-491. After the RNA thus obtained had been subjected to reverse transcription, amplification was allowed to proceed 30 cycles for one minute at 61° C., for two minutes at 72° C., and for 10 seconds at 95° C., respectively using PCR Primers (C11A and C11C, or C11B and C11C) which amplify the entire coding region for the c-erg gene. With either pair of the primers, two bands were obtained. Respective bands were cut out and DNA fragments were identified using a QiaexII gel extraction kit (Qiagen, Germany). These fragments were subcloned into a PCRII vector (Invitrogen, CA, USA), and then the full-length nucleotide sequences were determined by the Dideoxy method. As a result, a 1454 bp DNA fragment amplified with the primer pair of C11A and C11C completely matched the c-erg gene (Mechanism of Development (1995) 50: 17-28), whereas a 1373 bp DNA fragment turned out to be a sequence lacking 81 bases of from nucleotide 655 to nucleotide 735, from the c-erg gene. This novel sequence thus obtained was designated "C-11".

DNA fragments amplified using the primer pair of C11B and C11C were two kinds, namely 1446 bp and 1335 bp: the former fragment was c-erg and the latter was C-11. These results suggest the possibility that the thus obtained C-11 gene is an isoform of the c-erg gene.

It was also possible to isolate the aforementioned C-11 gene by a conventional subtraction method. Particularly, according to the subtraction method ordinarily known in the art, a cDNA which had specifically expressed in the embryonic sterna was cloned by employing a cDNA library of chicken embryonic sterna and fibroblasts. From the thus obtained candidate clones, genes were amplified by the PCR reaction using suitable primers to provide amplified gene products, the full nucleotide sequences of which were determined by standard techniques.

Results obtained with the aforementioned c-erg gene are shown through Example 2-1 to Example 2-8 as described below. In a like manner, experiments were conducted using the aforementioned C-11 gene and results therefrom are shown below, together with these for the c-erg gene.

EXAMPLE 2-1

Construction of a Vector Containing the c-erg Gene

The cloned c-erg as described above was subcloned into a RCAS vector (See, Journal of Virology (1987), October: 3004-3012) at its ClaI site in sense (c-erg) and antisense (AS-c-erg) directions, respectively. That they were indeed sense and antisense as described was confirmed by DNA sequencing.

The RCAS vector containing the subcloned c-erg and that containing the subcloned AS-c-erg were, respectively, introduced into chicken embryonic fibroblasts by the calcium phosphate co-precipitation method as described in Chen C. and Okayama H., Mol. Cell Diol. (1987), 7: 2745-2752. The vector-introduced cells were cultured for 48 hours at 37° C. on a DMEM medium containing 10% fetal bovine serum (The Nikken Biological Science Research Institute, Kyoto). Subsequently, virus produced in the culture supernatant was concentrated by means of a ultrafiltration membrane (molecular weight: 30,000 cut) (Centriprep available from Amicon Inc., MA, USA). This virus is herein referred to as "virus-CM".

In a like manner, only the RCAS vector was introduced into chicken embryonic fibroblasts and the virus recovered from the vector-introduced cells was used as a control.

A virus stock from the aforementioned chicken embryonic fibroblasts which was used in this invention was prepared by the method as described below.

Specifically, CEF was transfected with a DNA which had been obtained from RSV (Rous Sarcoma virus) by substitution of its v-src with a target gene by means of Calcium phosphate method and which contained a proviral structure with LTR at its both ends. The cells into which the genes were introduced, temporarily released a large quantity of virus. Then, the virus reached the state of propagation throughout the whole culture used in the transfection by virus infection. At this point, a virus stock was recovered from the culture medium. More specifically, CEF cells propagated in a confluent manner, which had been cultured 4-5 days after preparation, were inoculated in a 60 mm dish at $0.8 \times 10^6$ cells. On the following day, 10 μg of a DNA fragment or plasmid, each of which had been provided with a proviral structure, was introduced into the cells by transfection, according to the calcium phosphate co-precipitation method. The medium was made afresh one to two hours prior to transfection. Ten hours after transfection, the culture medium was washed three times with a standard medium and then the cells were allowed to propagate for two days. The whole culture transfected was passaged to a 90 mm dish and allowed to propagate for two additional days. The medium was made afresh and it was recovered as the virus stock after 48 hours. A new medium was again added to the culture medium and, after 12 hours, a virus stock was recovered for the second time.

EXAMPLE 2-2

Introduction of the c-erg Gene into Cells

The c-erg gene was introduced into chicken osteoblasts to observe the effects according to the method of Iwamoto et al. as described in J. Biol. Chem., (1993) 268(13): 9645-52. Parietal bones were excised from a chicken, 18 days old and osteoblasts for use were isolated from the bones by the method of Louis C. G. et al. as described in Developmental Biology (1987), 122: 49-60.

Virus-CM (and the control virus) prepared in Example 2-1 was added to the osteoblasts prepared as described above and virus infection was allowed to take place.

Whether or not the infection had occurred was determined by observing changes in the differentiation character of the cells. Infection efficiency toward virus cells was determined by staining the osteoblasts using a P19 antivirus antibody (Development Studies Hybridoma Bank) as described in Potts W. M. et al., J. Gen. Viol., (1982), 68: 3177-3182.

EXAMPLE 2-3

Morphological Observation of a Transformant with the c-erg Gene

The virus-infected osteoblasts obtained in Example 2-2 were observed under a phase contrast microscope with a magnification of 10. The result revealed that when compared with the cells in the control group, the virus-infected osteoblasts showed polygonal morphology in a smaller size (data not shown in the Drawings).

EXAMPLE 2-4

Detection of Expression of the c-erg Gene and C-11 Gene

To detect the expression of the aforementioned isoform, the C-11 gene, the RT-PCR method was performed according to the procedure as described below.

Figure 3:
FIG. 3 illustrates an autoradiograph of the gel electrophoresis results showing RT-PCR amplified products obtained in Example 2-4, where a 473 bp band and a 392 bp band, correspond to c-erg and C-11, respectively.

Total RNA was prepared from the pectus spinal tissue of chicken embryos, 18 days old by the method of Iwamoto et al. as described in Microscopy Research and Technique (1994), 28: 483-491. After converting this RNA into a DNA by means of a random hexamer and a superscript reverse transcriptase (both available from Gibco-BRL, MD, USA), the PCR amplification reaction was performed using Primers C11A and C11C (SEQ ID NO. 5 and SE ID NO. 7 set forth in the Sequence Listing) which had the nucleotide sequence for the ETA region (erg/ets transcription region) of the c-erg gene shown in FIG. 2, and that for the NRT region (transcription repressor region), respectively. In FIG. 2, the one that lacks 81 bases being flanked with the ETA and NRT domains is the C-11 gene. The thus obtained amplified products were subjected to electrophoresis on a 2% agarose gel and the results are shown in FIG. 3. These results revealed that the kinds of mRNA were amplified to show the isoform G11 gene as a 392 bp band together with the c-erg gene (as a 473 bp band).

EXAMPLE 2-5

Measurement of DNA Synthesizing Ability

The DNA synthesizing ability of the c-erg transformant cells was measured by the procedure described below.

After washing the cells with a cooled physiological saline solution three times, the cells were recovered from a physiological saline solution containing 0.01N NaOH and 0.2 v/v % Triton X-100. Upon recovery, the cells were crushed by ultrasonication and centrifuged to provide a supernatant which was used as a sample in the measurement. To 100 μl supernatant was added 200 μl of 0.1 g/ml DABA (3,5-diaminobenzoic acid dihydrochloride). After incubation for 45 minutes at 65° C. under a light-shielding condition, the reaction was terminated by adding 300 μl of 2N HCl. Upon termination of the reaction, fluorescence was monitored at wavelengths of 420 and 510 nm.

As used herein, "Rcas (or RCAS)" means the cells infected with the vector only. "c-erg-L14" means a RCAS into which a sense segment of the c-erg gene has been introduced. "c-erg-L44" means a RCAS into which an antisense segment of the c-erg gene has been introduced. Further, "C-11-L14" means a RCAS into which a sense segment of the C-11 gene has been introduced.

Figure 4:
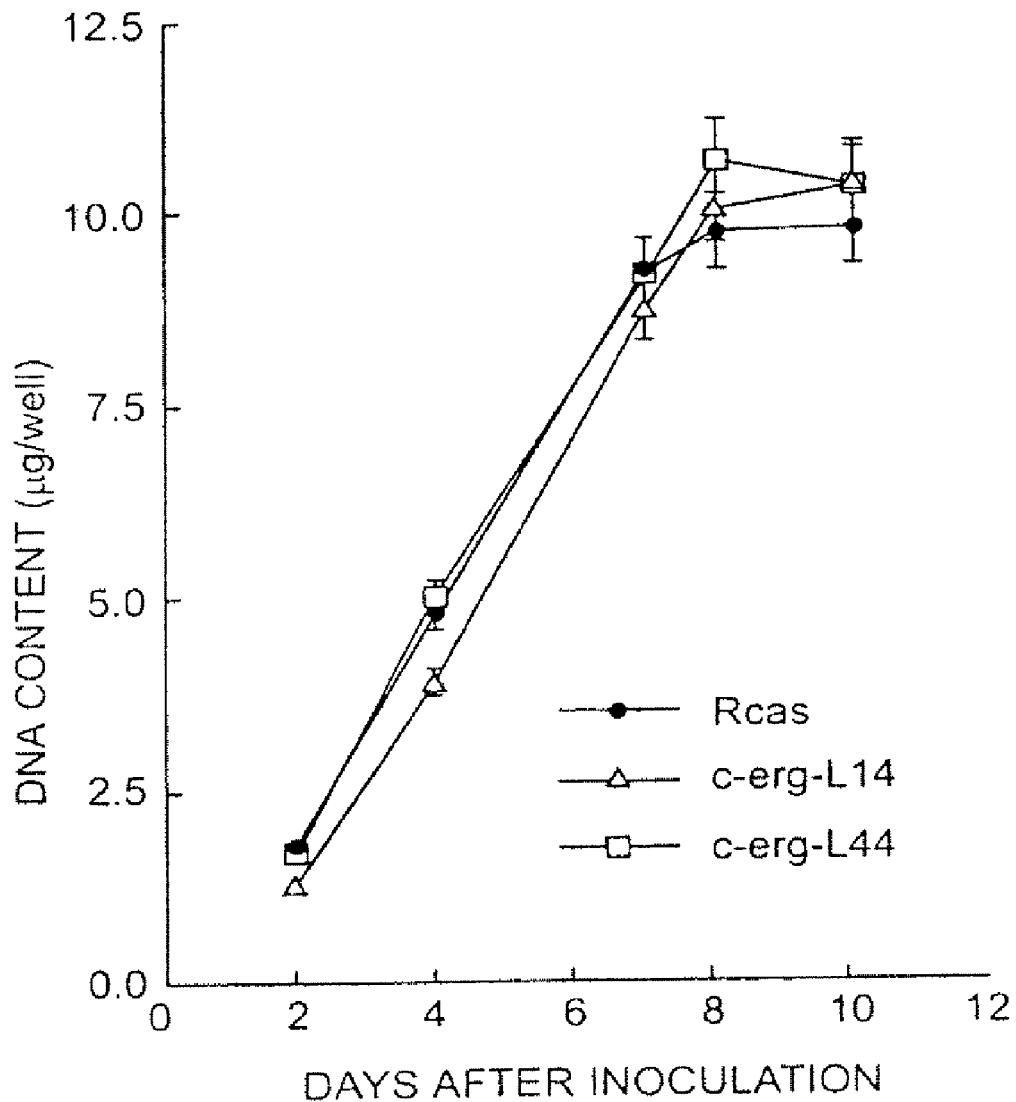
FIG. 4 illustrates the results comparing DNA synthesizing abilities of Rcas (osteoblasts infected with RCAS only), c-erg-L14 (osteoblasts infected with a c-erg sense segment-introduced RCAS), and c-erg-L44 (osteoblasts infected with a c-erg antisense segment-introduced RCAS).
Figure 5:
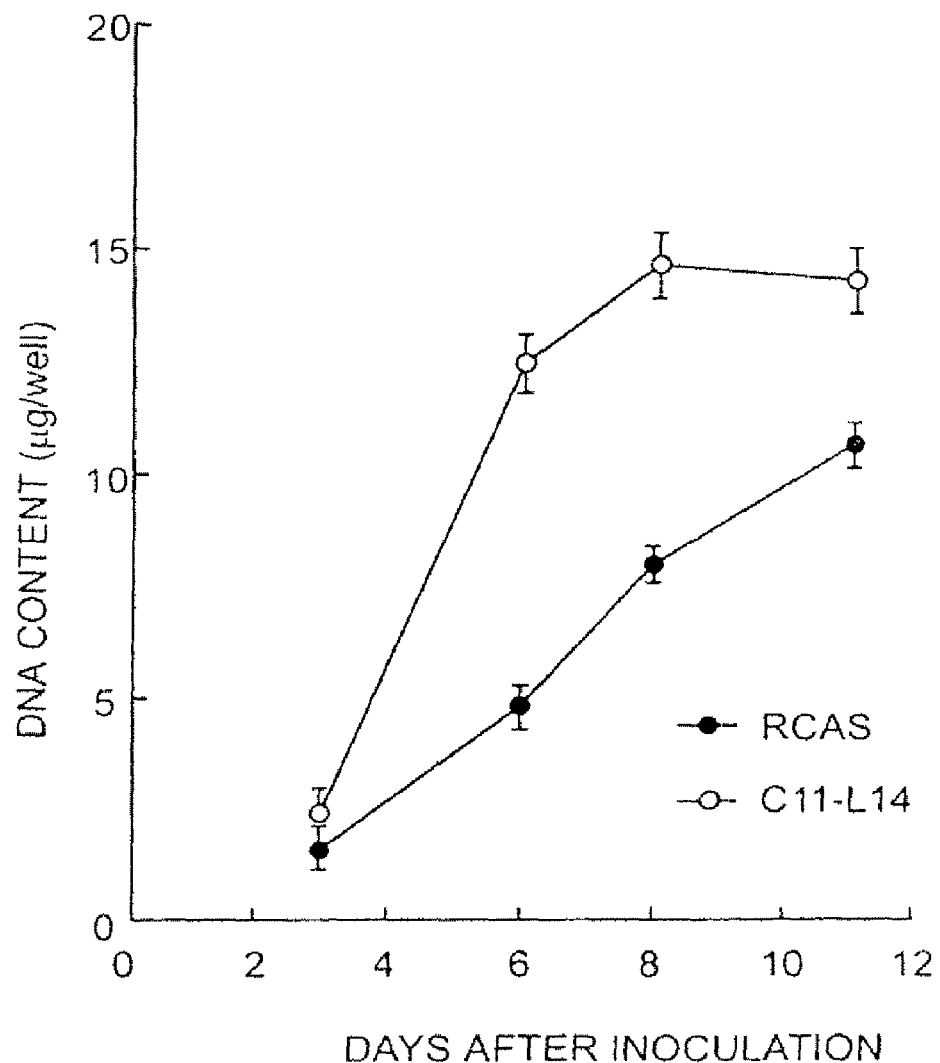
FIG. 5 illustrates the results comparing the DNA synthesizing abilities of Rcas (the osteoblasts infected with RCAS only) and C-11-L14 (osteoblasts infected with a C-11 sense segment-introduced RCAS).

As shown in FIG. 4, it was found that either of c-erg-L14 and c-erg-L44 (into both of which c-erg had been introduced) showed no significant difference in the DNA synthesizing ability as compared with RCAS (into which c-erg had not been introduced). In contrast, as shown in FIG. 5, it was found that C-11-L14 (into which C-11 had been introduced) showed a significant increase in the DNA synthesizing ability as compared with RCAS itself. This increase was particularly noted until day 6.

EXAMPLE 2-6

Measurement of Alkaline Phosphatase Activity

The alkaline phosphatase activity was measured according to the method of Kato Y, et al. as described in Endocrimology (1990), 127: 114-118.

Specifically, after washing the cells on ice with a cooled physiological saline solution three times, the cells were recovered from a physiological saline solution containing 0.2 v/v % Triton X-100. Upon recovery, the cells were crushed by ultrasonication and centrifuged to provide a supernatant which was used as a sample in the measurement.

The alkaline phosphatase activity of the supernatant was measured in 0.5M Tris/HCl buffer (pH 9.0) containing 0.5 mM pNP (para-nitrophenyl phosphate) and 0.5 mM $MgCl_2$. After incubating the mixed solution for 30 minutes at 37° C., the reaction was terminated by adding 0.25 volume of 1N NaOH. Upon termination of the reaction, absorbance was monitored at a wavelength of 410 nm.

Figure 6:
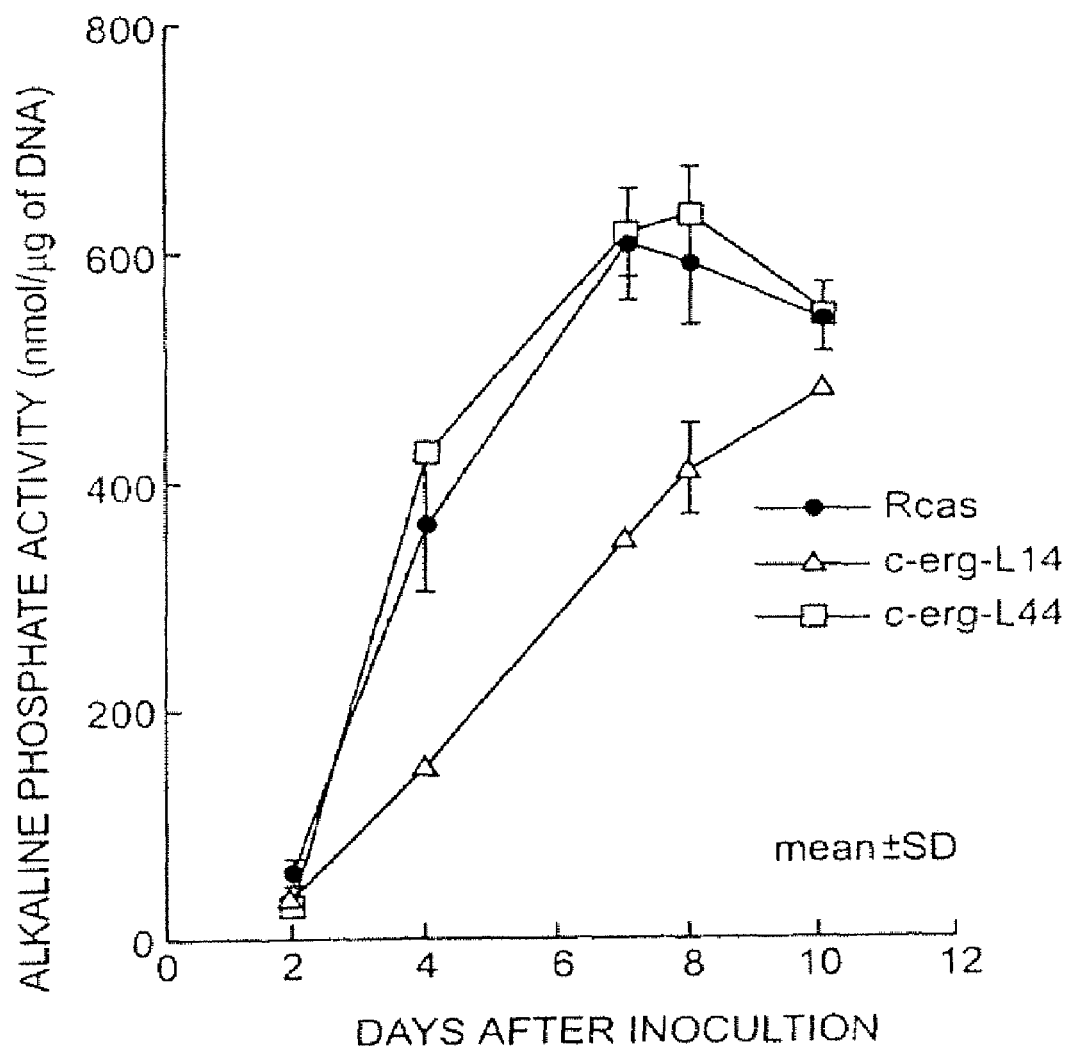
FIG. 6 illustrates the results comparing alkaline phosphatase activities of Rcas (the osteoblasts infected with only RCAS), c-erg-L14 (the osteoblasts infected with the c-erg sense segment-introduced RCAS) and c-erg-L44 (the osteoblasts infected with the c-erg antisense segment-introduced RCAS).

The results obtained employing RCAS, into which c-erg was introduced, are shown in FIG. 6. While no significant difference was observed between RCAS (which was the control) and c-erg-L44 (anti-sense segment introduced), the alkaline phosphatase activity of c-erg-L14 (sense-segment introduced) was found to be markedly inhibited.

Figure 7:
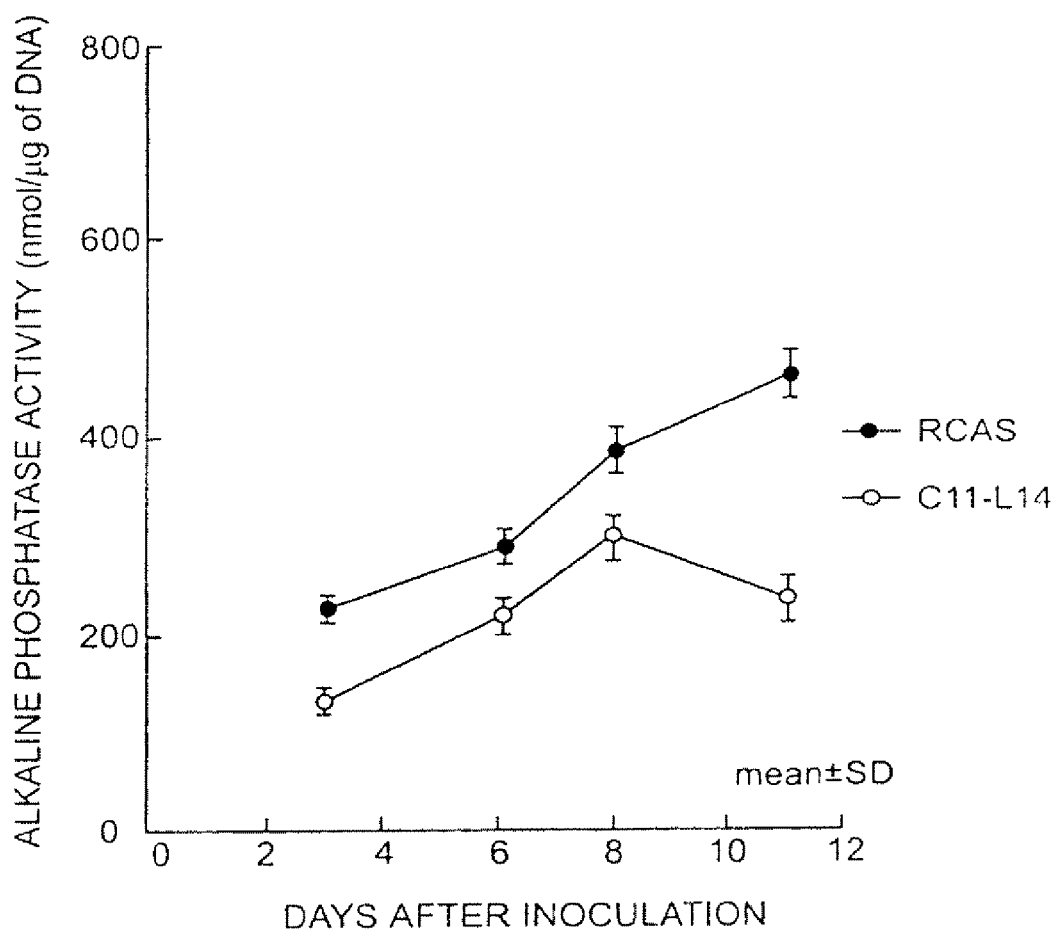
FIG. 7 illustrates the results comparing the alkaline phosphatase activities of Rcas (the osteoblasts infected with RCAS only) and C-11-L14 (the osteoblasts infected with the C-11 sense segment-introduced RCAS).

Similarly, the results obtained employing C-11-L14, into which a sense segment of the C-11 gene was introduced, are shown in FIG. 7. As compared with RCAS which was the control, the alkaline phosphatase activity of C-11-L14 was found to be markedly inhibited.

EXAMPLE 2-7

Alizarin Red Staining

After washing the cultured osteoblasts (on day 12 after inoculation) with PBS (phosphate buffer saline) twice the cells were fixed with 100% ethanol. After fixation, Alizarin Red S (sodium alizarin sulfonate available from Wako Pure Chemicals) was dissolved in distilled water and adjusted to pH 6.3-6.4 with 0.1 N $NH_3$, yielding a 1% Alizarin solution. This was added to the cells to effect staining for two minutes. After staining, the cells were washed with distilled water and air-dried.

Following the abovementioned operations, the calcification sites of the cells were stained reddish orange.

Figure 8:
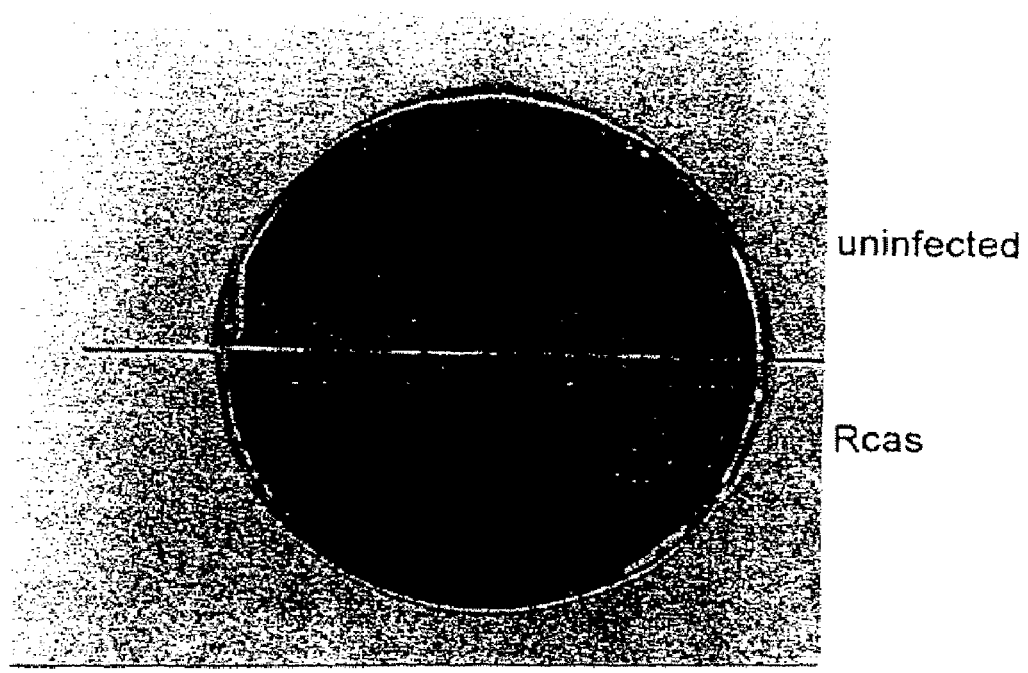
FIG. 8 illustrates a photograph showing the results on deposition of calcified products in a culture system consisting of uninfected osteoblasts (the upper half) and the osteoblasts infected with RCAS only (the lower half) as measured by the Alizarin Red staining.

FIG. 8 illustrates the results obtained by measuring the amount of deposition of calcified products in a culture system of the osteoblasts on day 19 after inoculation by means of Alizarin Red. Both uninfected cells and cells infected with the RCAS vector itself showed similar degrees of deposition of the calcified products. On the other hand, for c-erg-L14 (c-erg sense segment-introduced RCAS), the deposition was about half that for c-erg-L44 (c-erg anti-sense segment-introduced RCAS).

Figure 9:
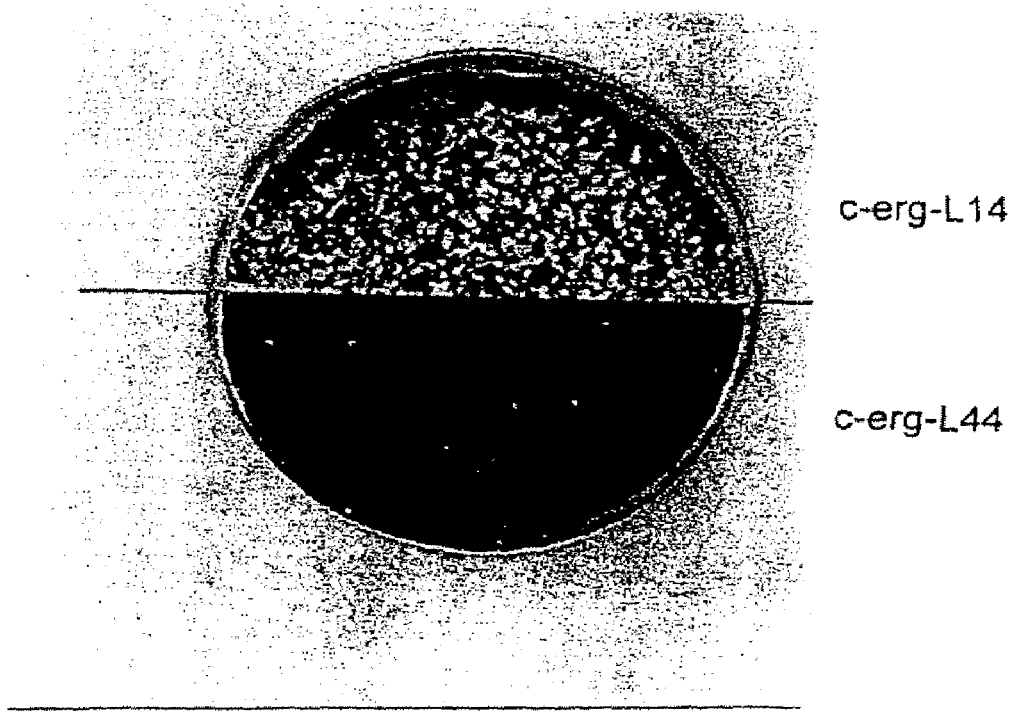
FIG. 9 illustrates a photograph showing the results on deposition of calcified products in a culture system consisting of the osteoblasts infected with c-erg-L14 RCAS (sense segment) (the upper half) and the osteoblasts infected with c-erg-L44 RCAS (antisense segment) (the lower half) as measured by the Alizarin Red staining.

Further, FIG. 9 illustrates that in the case of a C-11-L14 RCAS into which a sense segment of C-11 was introduced, almost no deposition of the calcified products was observed as the result of measurement with Alizarin Red.

Figure 10:
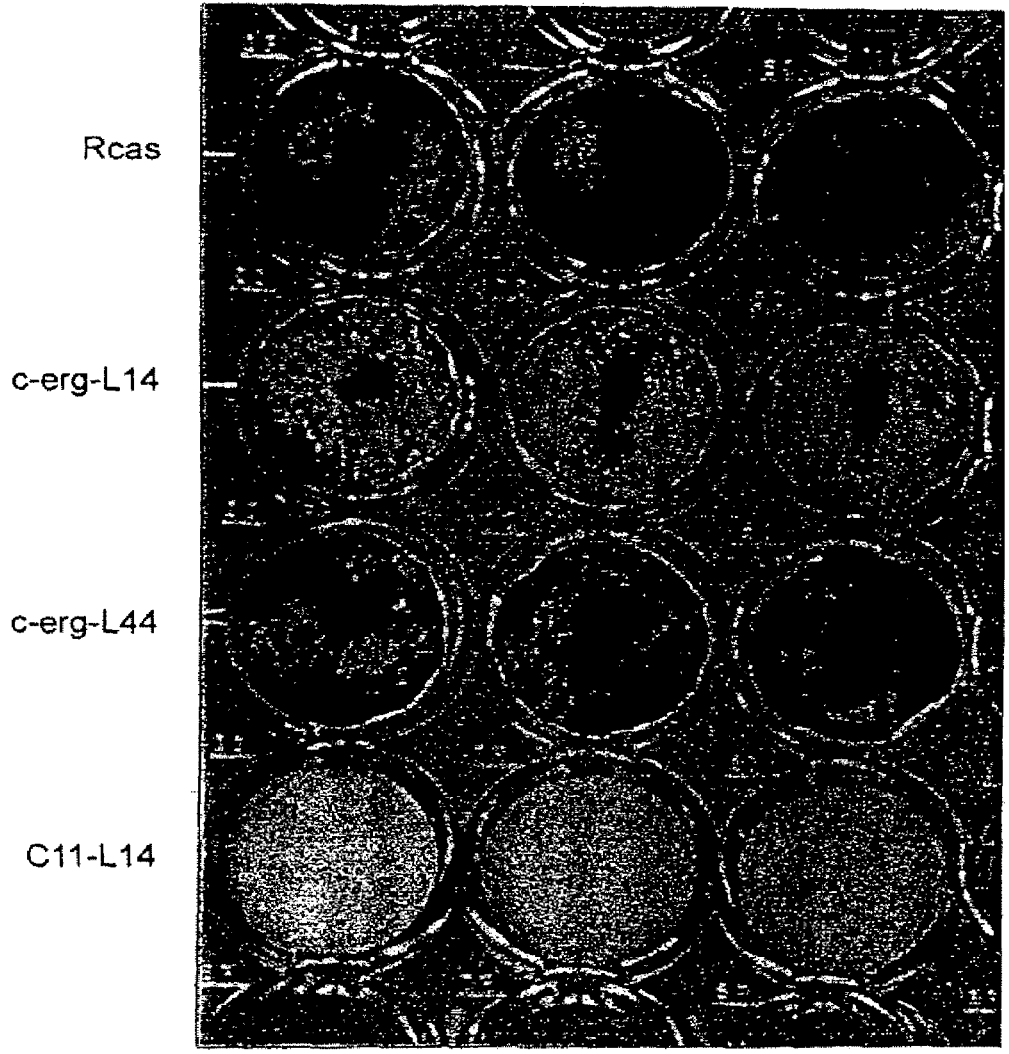
FIG. 10 illustrate a photograph showing the results on deposition of calcified products in a culture system consisting of the osteoblasts infected with RCAS only, the osteoblasts infected with c-erg-L14 RCAS (sense segment), the osteoblasts infected with c-erg-L44 RCAS (antisense segment), and the osteoblasts infected with C-11-L14 RCAS (sense segment) as measured by the Alizarin Red staining.
Figure 11:
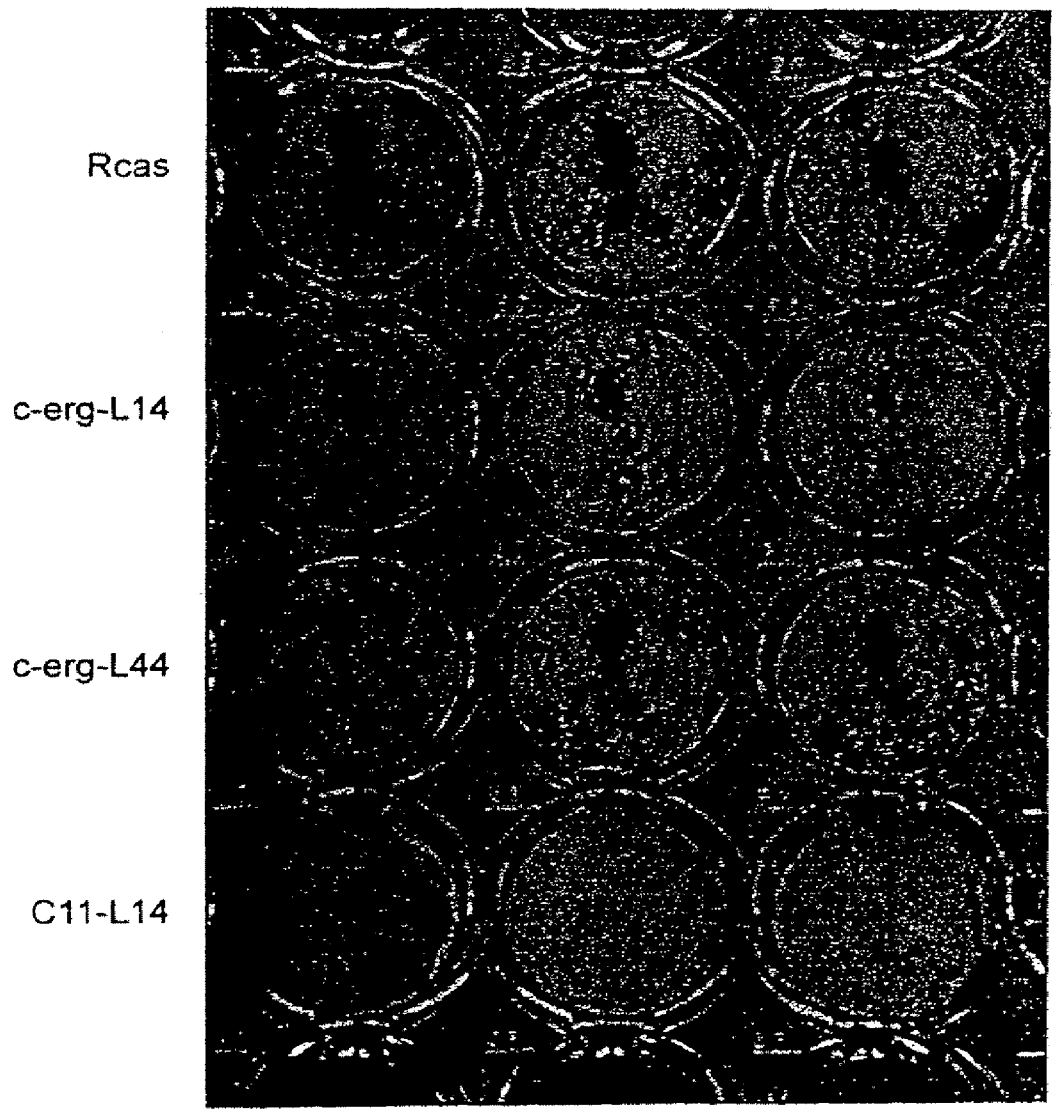
FIG. 11 illustrates a photograph showing the results on deposition of calcified products within cell nuclei in a culture system consisting of the osteoblasts infected with RCAS only, the osteoblasts infected with c-erg-L14 RCAS (sense segment), the osteoblasts infected with c-erg-L44 RCAS (antisense segment), and the osteoblasts infected with C-11-L14 RCAS (sense segment) as measured by the von Kossa staining (the right two columns) in addition to those obtained by double-staining the cell nuclei of the respective osteoblasts with Alum-carmine (the left column).

FIG. 10 illustrates the results from staining with Alizarin Red to compare the amounts of deposition of such calcified products. When compared under conditions where deposition of the calcified products was clearly observed in the cells infected with RCAS itself, c-erg L44 showed an extremely small inhibition on deposition of the calcified products. In contrast c-erg-L14 was found to nearly inhibit the deposition and C-11-L14 was found to almost completely inhibit the deposition.

EXAMPLE 2-8 von Kossa Staining

After washing the cultured osteoblasts (on day 12 after inoculation) with PBS twice, the cells were fixed with 100% ethanol. Then a 1% solution of silver nitrate was added to the cells and the solution was exposed to the sunlight for 30 minutes. Subsequently, the cells were washed with distilled water, to which a 5% aqueous solution of sodium thiosulfate was added. After allowing to stand for 5-10 minutes, the cells were washed with water. After washing, staining of cell nuclei was performed by adding an Alum-carmine solution and allowing to stand for 24 hours.

Following the abovementioned operations, the calcification sites of the cells were stained black, while the nuclei were stained crimson.

As in the Alizarin Red staining, with application of the von Kossa staining a lowered staining was observed and the deposition of the calcified products was inhibited in the c-erg-L14 group as compared with the control group (RCAS). Further, in the C-11-L14 group, the deposition was completely inhibited. The staining with Alum-carmine showed no discrimination among various groups. Therefore, the observed effects in this invention are not ascribable to variations in staining efficiency resulting from differences in the cell number, but are believed to be due to the fact that both c-erg-L14 and C-11-L14 functionally inhibit the calcification of the osteoblasts (amount of calcium deposited per cell).

What is claimed is:

1. An isolated C-11 protein consisting of an amino acid sequence of amino acids 198-451 from SEQ ID NO. 2, said protein having cell-calcification inhibitory activity.

2. A pharmaceutical composition comprising the protein according to claim 1.

3. The pharmaceutical composition according to claim 2, wherein said composition is intended for a cell-calcification inhibitor.

* * * * *

SEQUENCE LISTING

<160> NUMBER OF SEQ ID NOS: 7

<210> SEQ ID NO 1
<211> LENGTH: 1447
<212> TYPE: DNA
<213> ORGANISM: C-11 gene, c-erg gene w/ deletion, chicken DNA

<400> SEQUENCE: 1
gaattccgcg aacgaataat tattattagc aattattagc gatcaataat cttgatcaca      60

```
ttatggcaag cactattaag gaagcattat cagtggtgag tgaagaccag tccttgtttg    120
agtgtgccta cggatcgccc caccttgcaa agacagaaat gacagcctcc tcttccagtg    180
aatatgggca acatcaaag atgagcccgc gcgttcccca gcaggactgg ttatcacagc     240
ccccggccag agttaccatt aagatggagt gtaacccaaa ccaggttaat gggtcaagga    300
attcacctga tgactgcagc gtggcaaaag gagggaaaat ggttagcagt tcagacaatg    360
ttgggatgaa ctatggaagc tacatggaag agaagcatat tccgcctcca aatatgacaa    420
ccaatgaacg aagagttatt gtgccagcag atcctacgtt atggagcaca gaccatgtac    480
ggcagtggct ggagtgggca gtgaaggagt atggtcttcc agacgtggac atcttgttgt    540
tccagaacat tgatgggaaa gagttgtgta aaatgaccaa agatgacttc cagagactca    600
cgccgagcta taacgcagat atcctcctgt cacacctaca ctacctcaga gagagaggag    660 ccactttat ttttccaaat acatcagttt acccagaagc aacgcaaaga ataacaacaa     720
ggccagattt accttatgag caagcgagga gatcagcgtg gacgagtcac agccatccca    780
ctcagtcaaa agctacccaa ccatcatctt caacagtgcc caaaacagaa gaccagcgtc    840
ctcagttaga tccttatcag attcttggac cgaccagcag ccgtcttgca aatccaggga    900
gtgggcagat acagctatgg cagttcctac tggagcttct gtcggacagc tccaactcca    960
actgcatcac ctgggagggc acaaatgggg agttcaagat gacagaccct gatgaagtgg    1020
ctcggcgttg gggagagagg aaaagcaaac taacatgaa ctatgacaaa ctcagccgtg     1080
cacttcgcta ctactatgac aaaaatatta tgactaaagt tcatggtaaa cgctatgcct    1140
acaaatttga tttccacgga atcgctcagg ccctccagcc tcaccctcca gaatcatcca    1200
tgtacaaata cccatcagac ctcccctaca tgagttccta ccatgcacac cccagaagaa    1260
tgaactttgt agctccccat ccccctgctt tgcccgtaac ctcatccagc ttttttgctg    1320
cccctaatcc atactggaat tcaccaactg gaggcatcta ccccaatacc aggctgccag    1380
ctgctcatat gccttcccat cttggcacct actactaagt ggggaaagaa agaaagcgcc    1440
aagaaaa                                                             1447
```

<210> SEQ ID NO 2
<211> LENGTH: 451
<212> TYPE: PRT
<213> ORGANISM: protein sequence from C-11 gene

<400> SEQUENCE: 2

```
Met Ala Ser Thr Ile Lys Glu Ala Leu Ser Val Val Ser Glu Asp Gln
  1               5                  10                  15

Ser Leu Phe Glu Cys Ala Tyr Gly Ser Pro His Leu Ala Lys Thr Glu
             20                  25                  30

Met Thr Ala Ser Ser Ser Glu Tyr Gly Gln Thr Ser Lys Met Ser
         35                  40                  45

Pro Arg Val Pro Gln Gln Asp Trp Leu Ser Gln Pro Pro Ala Arg Val
     50                  55                  60

Thr Ile Lys Met Glu Cys Asn Pro Asn Gln Val Asn Gly Ser Arg Asn
 65                  70                  75                  80

Ser Pro Asp Asp Cys Ser Val Ala Lys Gly Gly Lys Met Val Ser Ser
                 85                  90                  95

Ser Asp Asn Val Gly Met Asn Tyr Gly Ser Tyr Met Glu Glu Lys His
            100                 105                 110

Ile Pro Pro Pro Asn Met Thr Thr Asn Glu Arg Arg Val Ile Val Pro
        115                 120                 125
```

Ala Asp Pro Thr Leu Trp Ser Thr Asp His Val Arg Gln Trp Leu Glu
    130                 135                 140

Trp Ala Val Lys Glu Tyr Gly Leu Pro Asp Val Asp Ile Leu Leu Phe
145                 150                 155                 160

Gln Asn Ile Asp Gly Lys Glu Leu Cys Lys Met Thr Lys Asp Asp Phe
                165                 170                 175

Gln Arg Leu Thr Pro Ser Tyr Asn Ala Asp Ile Leu Leu Ser His Leu
            180                 185                 190

His Tyr Leu Arg Glu Arg Gly Ala Thr Phe Ile Phe Pro Asn Thr Ser
        195                 200                 205

Val Tyr Pro Glu Ala Thr Gln Arg Ile Thr Thr Arg Pro Asp Leu Pro
    210                 215                 220

Tyr Glu Gln Ala Arg Arg Ser Ala Trp Thr Ser His Ser His Pro Thr
225                 230                 235                 240

Gln Ser Lys Ala Thr Gln Pro Ser Ser Ser Thr Val Pro Lys Thr Glu
                245                 250                 255

Asp Gln Arg Pro Gln Leu Asp Pro Tyr Gln Ile Leu Gly Pro Thr Ser
            260                 265                 270

Ser Arg Leu Ala Asn Pro Gly Ser Gly Gln Ile Gln Leu Trp Gln Phe
        275                 280                 285

Leu Leu Glu Leu Leu Ser Asp Ser Ser Asn Ser Asn Cys Ile Thr Trp
    290                 295                 300

Glu Gly Thr Asn Gly Glu Phe Lys Met Thr Asp Pro Asp Glu Val Ala
305                 310                 315                 320

Arg Arg Trp Gly Glu Arg Lys Ser Lys Pro Asn Met Asn Tyr Asp Lys
                325                 330                 335

Leu Ser Arg Ala Leu Arg Tyr Tyr Tyr Asp Lys Asn Ile Met Thr Lys
            340                 345                 350

Val His Gly Lys Arg Tyr Ala Tyr Lys Phe Asp Phe His Gly Ile Ala
        355                 360                 365

Gln Ala Leu Gln Pro His Pro Pro Glu Ser Ser Met Tyr Lys Tyr Pro
    370                 375                 380

Ser Asp Leu Pro Tyr Met Ser Ser Tyr His Ala His Pro Gln Lys Met
385                 390                 395                 400

Asn Phe Val Ala Pro His Pro Pro Ala Leu Pro Val Thr Ser Ser Ser
                405                 410                 415

Phe Phe Ala Ala Pro Asn Pro Tyr Trp Asn Ser Pro Thr Gly Gly Ile
            420                 425                 430

Tyr Pro Asn Thr Arg Leu Pro Ala Ala His Met Pro Ser His Leu Gly
        435                 440                 445

Thr Tyr Tyr
    450

<210> SEQ ID NO 3
<211> LENGTH: 1528
<212> TYPE: DNA
<213> ORGANISM: c-erg gene, chicken DNA

<400> SEQUENCE: 3
gaattccgcg aacgaataat tattattagc aattattagc gatcaataat cttgatcaca      60
ttatggcaag cactattaag gaagcattat cagtggtgag tgaagaccag tccttgtttg     120
agtgtgccta cggatcgccc caccttgcaa agacagaaat gacagcctcc tcttccagtg     180
aatatgggca acatcaaag atgagcccgc gcgttcccca gcaggactgg ttatcacagc     240

-continued

```
ccccggccag agttaccatt aagatggagt gtaacccaaa ccaggttaat gggtcaagga   300
attcacctga tgactgcagc gtggcaaaag gagggaaaat ggttagcagt tcagacaatg   360
ttgggatgaa ctatggaagc tacatggaag agaagcatat tccgcctcca aatatgacaa   420
ccaatgaacg aagagttatt gtgccagcag atcctacgtt atggagcaca gaccatgtac   480
ggcagtggct ggagtgggca gtgaaggagt atggtcttcc agacgtggac atcttgttgt   540
tccagaacat tgatgggaaa gagttgtgta aaatgaccaa agatgacttc agagactca    600
cgccgagcta taacgcagat atcctcctgt cacacctaca ctacctcaga gagactcctc   660
ttccacattt gacttcagat gatgttgata aggccttaca aaactctcca cggttaatgc   720
atgctagaaa cacaggagga gccactttta tttttccaaa tacatcagtt tacccagaag   780
caacgcaaag aataacaaca aggccagatt taccttatga gcaagcgagg agatcagcgt   840
ggacgagtca cagccatccc actcagtcaa aagctaccca accatcatct tcaacagtgc   900
ccaaaacaga agaccagcgt cctcagttag atccttatca gattcttgga ccgaccagca   960
gccgtcttgc aaatccaggg agtgggcaga tacagctatg gcagttccta ctggagcttc  1020
tgtcggacag ctccaactcc aactgcatca cctgggaggg cacaaatggg gagttcaaga  1080
tgacagaccc tgatgaagtg gctcggcgtt ggggagagag gaaaagcaaa cctaacatga  1140
actatgacaa actcagccgt gcacttcgct actactatga caaaaatatt atgactaaag  1200
ttcatggtaa acgctatgcc tacaaatttg atttccacgg aatcgctcag gccctccagc  1260
ctcacccctcc agaatcatcc atgtacaaat acccatcaga cctcccctac atgagttcct  1320
accatgcaca ccccccagaag atgaactttg tagctcccca tccccctgct ttgcccgtaa  1380
cctcatccag cttttttgct gccccctaatc catactggaa ttcaccaact ggaggcatct  1440
accccaatac caggctgcca gctgctcata tgccttccca tcttggcacc tactactaag  1500
tggggaaaga aagaaagcgc caagaaaa                                     1528
```

<210> SEQ ID NO 4
<211> LENGTH: 478
<212> TYPE: PRT
<213> ORGANISM: protein sequence from c-erg gene

<400> SEQUENCE: 4

```
Met Ala Ser Thr Ile Lys Glu Ala Leu Ser Val Ser Glu Asp Gln
  1               5                  10                  15

Ser Leu Phe Glu Cys Ala Tyr Gly Ser Pro His Leu Ala Lys Thr Glu
                 20                  25                  30

Met Thr Ala Ser Ser Ser Glu Tyr Gly Gln Thr Ser Lys Met Ser
             35                  40                  45

Pro Arg Val Pro Gln Gln Asp Trp Leu Ser Gln Pro Ala Arg Val
     50                  55                  60

Thr Ile Lys Met Glu Cys Asn Pro Asn Gln Val Asn Gly Ser Arg Asn
 65                  70                  75                  80

Ser Pro Asp Asp Cys Ser Val Ala Lys Gly Gly Lys Met Val Ser Ser
                     85                  90                  95

Ser Asp Asn Val Gly Met Asn Tyr Gly Ser Tyr Met Glu Glu Lys His
                100                 105                 110

Ile Pro Pro Pro Asn Met Thr Thr Asn Glu Arg Arg Val Ile Val Pro
             115                 120                 125

Ala Asp Pro Thr Leu Trp Ser Thr Asp His Val Arg Gln Trp Leu Glu
    130                 135                 140

Trp Ala Val Lys Glu Tyr Gly Leu Pro Asp Val Asp Ile Leu Leu Phe
```

```
            145                 150                 155                 160
Gln Asn Ile Asp Gly Lys Glu Leu Cys Lys Met Thr Lys Asp Asp Phe
            165                 170                 175

Gln Arg Leu Thr Pro Ser Tyr Asn Ala Asp Ile Leu Leu Ser His Leu
            180                 185                 190

His Tyr Leu Arg Glu Thr Pro Leu Pro His Leu Thr Ser Asp Asp Val
            195                 200                 205

Asp Lys Ala Leu Gln Asn Ser Pro Arg Leu Met His Ala Arg Asn Thr
210                 215                 220

Gly Gly Ala Thr Phe Ile Phe Pro Asn Thr Ser Val Tyr Pro Glu Ala
225                 230                 235                 240

Thr Gln Arg Ile Thr Thr Arg Pro Asp Leu Pro Tyr Glu Gln Ala Arg
            245                 250                 255

Arg Ser Ala Trp Thr Ser His Ser His Pro Thr Gln Ser Lys Ala Thr
            260                 265                 270

Gln Pro Ser Ser Thr Val Pro Lys Thr Glu Asp Gln Arg Pro Gln
            275                 280                 285

Leu Asp Pro Tyr Gln Ile Leu Gly Pro Thr Ser Ser Arg Leu Ala Asn
290                 295                 300

Pro Gly Ser Gly Gln Ile Gln Leu Trp Gln Phe Leu Leu Glu Leu Leu
305                 310                 315                 320

Ser Asp Ser Ser Asn Ser Asn Cys Ile Thr Trp Glu Gly Thr Asn Gly
            325                 330                 335

Glu Phe Lys Met Thr Asp Pro Asp Glu Val Ala Arg Arg Trp Gly Glu
            340                 345                 350

Arg Lys Ser Lys Pro Asn Met Asn Tyr Asp Lys Leu Ser Arg Ala Leu
            355                 360                 365

Arg Tyr Tyr Tyr Asp Lys Asn Ile Met Thr Lys Val His Pro Pro Glu
            370                 375                 380

Ser Ser Met Tyr Lys Tyr Pro Ser Asp Leu Pro Tyr Met Ser Ser Tyr
385                 390                 395                 400

His Gly Lys Arg Tyr Ala Tyr Lys Phe Asp Phe His Gly Ile Ala Gln
            405                 410                 415

Ala Leu Gln Pro His Ala His Pro Gln Lys Met Asn Phe Val Ala Pro
            420                 425                 430

His Pro Pro Ala Leu Pro Val Thr Ser Ser Phe Phe Ala Ala Pro
            435                 440                 445

Asn Pro Tyr Trp Asn Ser Pro Thr Gly Gly Ile Tyr Pro Asn Thr Arg
450                 455                 460

Leu Pro Ala Ala His Met Pro Ser His Leu Gly Thr Tyr Tyr
465                 470                 475

<210> SEQ ID NO 5
<211> LENGTH: 23
<212> TYPE: DNA
<213> ORGANISM: primer for isolation of C-11 and c-erg genes

<400> SEQUENCE: 5
atcttgatca cattatggca agc                                            23

<210> SEQ ID NO 6
<211> LENGTH: 25
<212> TYPE: DNA
<213> ORGANISM: primer for isolation of C-11 and c-erg genes

<400> SEQUENCE: 6
```

```
cacattatgg caagcactat taagg                                            25

<210> SEQ ID NO 7
<211> LENGTH: 25
<212> TYPE: DNA
<213> ORGANISM: primer for isolation of C-11 and c-erg genes

<400> SEQUENCE: 7
cacttagtag taggtgccaa gatgg                                            25
```